(12) United States Patent
Madabhushi et al.

(10) Patent No.: US 10,049,770 B2
(45) Date of Patent: Aug. 14, 2018

(54) PREDICTION OF RECURRENCE OF NON-SMALL CELL LUNG CANCER

(71) Applicant: Case Western Reserve University, Cleveland, OH (US)

(72) Inventors: Anant Madabhushi, Shaker Heights, OH (US); Xiangxue Wang, Cleveland, OH (US); Vamsidhar Velcheti, Pepper Pike, OH (US)

(73) Assignee: Case Western Reserve University, Cleveland, OH (US)

( * ) Notice: Subject to any disclaimer, the term of this patent is extended or adjusted under 35 U.S.C. 154(b) by 29 days.

(21) Appl. No.: 15/389,845

(22) Filed: Dec. 23, 2016

(65) Prior Publication Data

US 2017/0193175 A1    Jul. 6, 2017

Related U.S. Application Data

(60) Provisional application No. 62/272,774, filed on Dec. 30, 2015.

(51) Int. Cl.
*G06T 7/00* (2017.01)
*G06K 9/00* (2006.01)
(Continued)

(52) U.S. Cl.
CPC ........... *G16H 50/20* (2018.01); *G06F 19/345* (2013.01); *G06K 9/3233* (2013.01);
(Continued)

(58) Field of Classification Search
CPC ........ G06T 2207/30096; G06T 7/0012; G06T 7/11; G06T 2207/30024;
(Continued)

(56) References Cited

U.S. PATENT DOCUMENTS

2005/0262031 A1\* 11/2005 Saidi ...................... G16H 50/20
706/21
2007/0099219 A1\* 5/2007 Teverovskiy .......... G16H 50/50
435/6.16

(Continued)

OTHER PUBLICATIONS

D. Song, T. A. Zhukov, O. Markov, W. Qian and M. S. Tockman, "Prognosis of stage I lung cancer patients through quantitative analysis of centrosomal features," 2012 9th IEEE International Symposium on Biomedical Imaging (ISBI), Barcelona, 2012, pp. 1607-1610.\*
U.S. Appl. No. 15/389,872, filed Dec. 23, 2016.
Notice of Allowance received May 21, 2018 in connection with U.S. Appl. No. 15/389,872.

*Primary Examiner* — Utpal Shah
(74) *Attorney, Agent, or Firm* — Eschweiler & Potashnik, LLC

(57) ABSTRACT

Methods, apparatus, and other embodiments associated with predicting non-small cell lung cancer (NSCLC) patient response to adjuvant chemotherapy therapy using radiomic features extracted from digitized hematoxylin and eosin (H&E) stained slides of a region of tissue demonstrating NSCLC. One example apparatus includes an image acquisition circuit that acquires an H&E image of a region of tissue demonstrating NSCLC pathology, a segmentation circuit that segments a region of interest (ROI) from the diagnostic radiological image, a feature extraction that extracts a set of discriminative features from the ROI, and a classification circuit that generates a probability that the ROI will experience NSCLC recurrence. The classification circuit may compute a quantitative continuous image-based risk score based on the probability or the image. A prognosis or treatment plan may be provided based on the quantitative continuous image-based risk score.

20 Claims, 8 Drawing Sheets

(51) Int. Cl.
  *G16H 50/20* (2018.01)
  *G06F 19/00* (2018.01)
  *G06N 3/08* (2006.01)
  *G06N 3/04* (2006.01)
  *G06T 7/11* (2017.01)
  *G06K 9/62* (2006.01)
  *G06K 9/32* (2006.01)
  *G06K 9/66* (2006.01)

(52) U.S. Cl.
  CPC ......... *G06K 9/6277* (2013.01); *G06K 9/6281* (2013.01); *G06K 9/6286* (2013.01); *G06K 9/6287* (2013.01); *G06K 9/66* (2013.01); *G06N 3/0472* (2013.01); *G06N 3/08* (2013.01); *G06T 7/0012* (2013.01); *G06T 7/11* (2017.01); *G06T 2207/10004* (2013.01); *G06T 2207/20036* (2013.01); *G06T 2207/20081* (2013.01); *G06T 2207/30061* (2013.01); *G06T 2207/30096* (2013.01)

(58) Field of Classification Search
  CPC ........... G06T 2207/20036; G06T 2207/30061; G06K 9/3233; G06K 9/6267
  See application file for complete search history.

(56) References Cited

U.S. PATENT DOCUMENTS

| | | | |
|---|---|---|---|
| 2012/0010528 A1* | 1/2012 | Donovan | G06K 9/00147 600/567 |
| 2012/0177280 A1* | 7/2012 | Zhukov | G01N 33/5076 382/133 |
| 2013/0080134 A1* | 3/2013 | Donovan | G06F 17/30477 703/11 |
| 2015/0310632 A1* | 10/2015 | Banerjee | G06K 9/6267 382/131 |
| 2017/0103521 A1 | 4/2017 | Chukka | |

\* cited by examiner

PREDICTION OF RECURRENCE OF NON-SMALL CELL LUNG CANCER

CROSS REFERENCE TO RELATED APPLICATIONS

This application claims the benefit of U.S. Provisional Application 62/272,774 filed Dec. 30, 2015.

BACKGROUND

Non-small cell lung cancer (NSCLC) accounts for approximately 85% of all lung cancers experienced by patients, leading to large numbers of cancer related deaths around the world. While the stage of NSCLC is frequently used to determine the type of treatment administered to an NSCLC patient, surgical resection of tumor tissue still remains a leading option for early stage NSCLC. Although some patients who undergo surgical resection of tumor tissue will be cured, a significant subset of patients who under surgical resection will develop a recurrence of NSCLC and subsequently die from the disease. Adjuvant treatment with platinum based doublet chemotherapy (adjuvant chemotherapy) is the standard of care for NSCLC patients following surgical resection. However, a majority of these patients will not receive any additional benefit from the adjuvant chemotherapy, and will instead be subjected to unnecessary suffering and other deleterious effects. Additionally, a substantial portion of the over $12 billion spent annually in the United States on lung cancer care is directed to unnecessary treatment.

There are no prospectively validated and clinically relevant conventional tools to predict the additional benefit of post-surgery adjuvant chemo for early stage NSCLC. Conventional tests for NSCLC are mainly prognostic, and there are no established molecular diagnostic assays for NSCLC that have been validated in terms of their predictive ability. Furthermore, conventional prognostic approaches are often not reimbursed and thus have poor market penetration. Conventional predictive molecular tests are also expensive, involve tissue destruction, and require specialized facilities. Conventional predictive approaches also have turnaround times from 10-14 days to up to several weeks, which are not clinically optimal time frames. Additionally, conventional molecular tests rely on small regions of tissue for profiling genes and proteins, and therefore do not comprehensively characterize the tumor being examined.

Conventional predictive approaches to separating NSCLC patients into low-risk or high-risk categories rely on the visual evaluation by a human pathologist of hematoxylin and eosin (H&E) stained images of lung biopsy specimens. A pathologist may manually identify, count, and grade tumor infiltrating lymphocytes (TIL) in a tumor. High densities of TILs are associated with survival for certain cancers. However, since TILs are identified, counted, and graded manually, conventional approaches to assessing risk in NSCLC patients are subjective, error prone, and suffer from inter-rater reliability issues. Since human pathologists may be challenged to reliably assess the risk of NSCLC recurrence using conventional approaches in clinically relevant time frames, ineffective therapies and procedures may be performed that ultimately result in poor outcomes for the patient. Thus, it would be beneficial if a faster, less costly, more reliable, automated approach to predicting the recurrence of NSCLC in patients were available.

BRIEF DESCRIPTION OF THE DRAWINGS

The accompanying drawings, which are incorporated in and constitute a part of the specification, illustrate various example apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
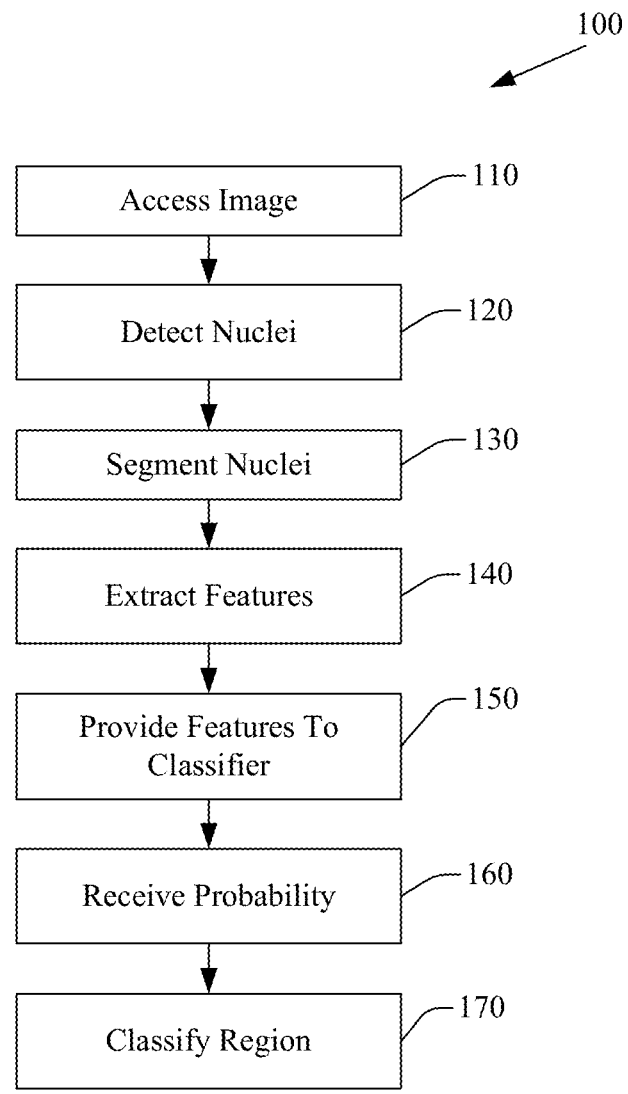
FIG. 1 illustrates an example method for predicting recurrence of NSCLC.

NSCLC accounts for approximately 85% of all lung cancers. Even though many early stage NSCLC patients are treated with adjuvant chemotherapy following surgical resection of NSCLC tumor tissue, the majority of these early-stage NSCLC patients do not receive any additional benefit from the adjuvant chemotherapy. Post-surgery recurrence is a key reason for treatment failure in early stage NSCLC, including stage 1 NSCLC, and stage 2 NSCLC. Variations in tumor morphology, and in tumor-infiltrating lymphocyte (TIL) density and architecture are associated with NSCLC recurrence. For example, higher densities of TILs have been associated with improved survival rates for NSCLC patients. However, TIL counting and grading is conventionally performed manually by a human pathologist. Conventional approaches to predicting NSCLC recurrence based on TIL density are therefore slow, subjective, and subject to high inter-observer disagreement. Thus, a faster, automated, accurate approach to predicting NSCLC recurrence in patients would be beneficial.

Example methods and apparatus utilize tumor morphology represented in digitized images of H&E stained slides to characterize NSCLC tumors. Tumor morphology reflects a sum of temporal genetic, epigenetic, proteomic, and metabolic changes and alterations in tumor cells. Tumor morphology thus provides useful information for predicting tumor biology, clinical behavior, or treatment response. For example, intra-tumoral morphologic heterogeneity is often a reflection of the tumor's molecular heterogeneity. Heterogeneous NSCLC tumors tend to be more aggressive, and most benefit from adjuvant chemotherapy. Additionally, the presence of TILs is associated with longer overall patient survival. In different tumors, immune cell (e.g. TIL) subpopulations are strategically distributed within different tissue compartments (e.g. epithelium, stroma), indicating that different TIL architectures have different biological roles and predict different outcomes in tumor control.

Example methods and apparatus predict recurrence of early stage NSCLC by quantitatively characterizing tumor morphology, TIL spatial architecture, or TIL density in a region of tissue demonstrating cancerous pathology. Example methods and apparatus extract nuclear morphological features from an image of the region of tissue demonstrating NSCLC. Example methods and apparatus may segment TILs from stromal or epithelial regions represented in the image. Example methods and apparatus facilitate detailed quantitative spatial interrogation of a tumor's morphologic landscape and invasive elements represented in a digitized H&E slide. Example methods and apparatus extract quantitative information about nuclear orientation, texture, shape, architecture, density, or patterns of stromal or epithelial TILs from the digitized H&E slide. Example methods and apparatus may train a classifier to predict recurrence in early stage NSCLC based on the quantitative information, which may include TIL density, architecture, or nuclear morphology features. Example methods and apparatus also distinguish NSCLC patients with early stage NSCLC as likely to suffer early recurrence from those NSCLC patients likely to experience longer disease free survival times. Example methods and apparatus may generate a quantitative, continuous, image-based risk score that provides clinically actionable information about additional benefit from adjuvant chemotherapy for early stage NSCLC patients based, at least in part, on the tumor morphology or spatial architecture and density of TILs represented in the image. For example, in one embodiment, a risk score may be based on tumor morphology. In another embodiment, the risk score may be based on TIL density or spatial architecture. In another embodiment, the risk score may be based on TIL density or spatial architecture, and on tumor morphology.

Example methods and apparatus predict patient outcomes more accurately than conventional methods by employing a quadratic discriminant analysis (QDA) of extracted features associated with TIL density or nuclear morphology. Example methods and apparatus may employ independently collected tissue microarrays to train and test a machine learning classifier, including an automated deep learning classifier, to predict NSCLC recurrence. Example methods and apparatus may predict recurrence of NSCLC with an accuracy of at least 0.68 area under the curve (AUC) when using a classifier trained on TIL density features. Example methods and apparatus may predict recurrence of NSCLC with an accuracy of at least 0.71 AUC when employing a classifier trained on texture and shape features extracted from a set of digitized H&E stained images of lung biopsy specimens.

In one embodiment, NSCLC recurrence is predicted based on TIL density features extracted from an H&E stained image of a region of tissue demonstrating NSCLC pathology. In this embodiment, a first set of 70 digitized H&E stained images of lung biopsy specimens from patients known to have experienced NSCLC recurrence or NSCLC non-recurrence is used to train a machine learning classifier to predict NSCLC recurrence. Training the classifier may include determining an optimal threshold risk score that separates low and high recurrence rates based on the training set. The training set may be divided into two groups: those who experience recurrence (Rc+) and those that did not experience recurrence (Rc−). In one embodiment, the optimal threshold may be determined such that 7% of the Rc+ patients have a risk score below the threshold. Thus, a risk score less than the threshold indicates low risk of recurrence, suggesting a recommended treatment of no adjuvant chemotherapy after surgical resection, while risk scores above the threshold indicate a high risk of recurrence, suggesting a recommended treatment of adjuvant chemotherapy after resection. A level of treatment aggressiveness may be based, at least in part, on the risk score.

In this embodiment, a second, different testing set of 119 digitized H&E stained images of lung biopsy specimens is used to test and independently validate the trained classifier. Other sizes of sets of digitized H&E stained images may be used. The testing set includes a low risk subset of images of a region of NSCLC tissue that did not experience recurrence, and a high risk subset of images a region of NSCLC tissue that did experience recurrence. Testing the classifier may include determining that the classifier has not more than a 50% false positive error rate with the low risk of recurrence NSCLC testing subset, and not more than a 7% false negative error rate with the high risk testing subset.

The machine learning classifier may be a QDA classifier, or other type of machine learning classifier, including a linear discriminant analysis (LDA) classifier, a support vector machine (SVM), or a random forest classifier. A cell represented in a diagnostic image or a member of the set of testing or training images is segmented from the background of the image. The cell may be segmented using a watershed technique, or may be segmented using another, different technique. For example, the cell may be segmented manually, or the cell may be segmented using a convolutional neural network approach or a region growing approach. Example methods and apparatus extract shape or color features from the image, including extracting features from the segmented cell. Lymphocytes or TILs may be identified based, at least in part, on the extracted shape or color features. The shape or color features may include a median red channel value feature.

Example methods and apparatus may construct a lymphocyte or TIL cluster using the identified lymphocytes, and generate a graph of the lymphocyte cluster. Individual lymphocytes are used as vertexes of the graph, where the distance between a first lymphocyte and a second, different lymphocyte is used as an edge value. Example methods and apparatus may employ a cell cluster graph (CCG) approach to generate the graph of the lymphocyte cluster. Example methods and apparatus extract a set of statistical features from the graph, including a mean lymphocyte density and maximum lymphocyte density. The set of statistical features may also include a number of nodes, an edge length, a degree, a number of edges, a cyclomatic number, a number of triangles, a number of k-walks, a spectral radius, an Eigen exponent, a Wiener index, an eccentricity, a Randic index, or a fractal dimension. A risk score may be computed based on the graph, or the set of statistical features extracted from the graph.

In another embodiment, example methods and apparatus predict NSCLC recurrence based on architectural features of individual cancer nuclei in the image. Example methods and apparatus may generate a graph of the individual cancer nuclei. Individual cancer nuclei are used as vertexes of the graph, where the distance between a first cancer nucleus and a second, different nucleus is used as an edge value. Example methods and apparatus may employ a cell cluster graph (CCG) approach to generate the graph of the cancer nuclei. Example methods and apparatus extract a set of statistical features from the graph. The set of statistical features may also include a number of nodes, an edge length, a degree, a number of edges, a cyclomatic number, a number of triangles, a number of k-walks, a spectral radius, an Eigen exponent, a Wiener index, an eccentricity, a Randic index, or a fractal dimension. A risk score may be computed based on the graph, or the set of statistical features extracted from the graph.

In another embodiment, NSCLC recurrence is predicted based on textural and shape features extracted from an H&E stained image of a region of tissue demonstrating NSCLC pathology. In this embodiment, a first set of 46 digitized H&E stained images of lung biopsy specimens is used to train a machine learning classifier to predict NSCLC recurrence. Example methods and apparatus detect nuclei from within a member of the first set. The nuclei may be detected automatically using a deep learning approach, or may be detected by a human pathologist. A deep learning approach is a machine learning approach that learns maximally differentiating feature representations directly from a data set to dichotomize instances into a first class or a second class. In a deep learning approach, discriminative features are not pre-specified, but are learned directly from the raw input data.

Example methods and apparatus segment nuclei from the background of the image. The nuclei may be segmented automatically, or may be segmented by a human pathologist. Example methods and apparatus extract a set of features from the segmented nuclei. The set of features may include texture features or shape features. The texture features may include a Haralick feature, and the shape features may include a median fractal dimension feature. The set of features may include features that are invariant to color. Example methods and apparatus may train a machine learning classifier using the set of features. The machine learning classifier may be a random forest classifier, or other type of machine learning classifier. The machine learning classifier may classify the region represented in the image as likely to experience NSCLC recurrence, or unlikely to experience NSCLC recurrence, based on the set of features. A risk score may be computed based on the classification of the image.

Example methods and apparatus may train and test an automated deep learning classifier. The classifier may be a random forest classifier, a QDA classifier, linear discriminant analysis (LDA) classifier, an SVM classifier, or other type of machine-learning based classifier. In one embodiment in which NSCLC recurrence is predicted based on textural and shape features, example methods and apparatus employ a set of training images of tissue demonstrating NSCLC for training the classifier, and a set of testing images for testing the classifier. For example, a human pathologist may manually delineate and classify a first set of 46 digitized images of H&E stained lung biopsy specimens for a training set and a second set of 69 digitized images of H&E stained lung biopsy specimens for a testing set. Example methods and apparatus may then train the classifier using the training set and test the classifier using the testing set to classify a region of tissue as likely to experience NSCLC recurrence or unlikely to experience NSCLC recurrence. Other sizes of training sets or sizes of testing sets may be employed.

Some conventional approaches for predicting NSCLC recurrence, including immunohistochemistry (IHC) based tests, suffer from problems related to quantitation, pre-analytics, reproducibility, or calibration. Example methods and apparatus employ color standardization or stain-invariant feature analysis schemes. Color standardization and stain invariant analysis facilitate robustness to variations in slide preparation or slide staining. Color standardization may include non-linearly correcting drift in color within tissue compartments. Stain-invariant analysis may include nuclear and cell segmentation that employs stain normalization using sparse autoencoders. By employing color standardization and stain invariant analysis, example methods and apparatus facilitate using images acquired from different institutions, or from different types of image acquisition systems.

Example methods and apparatus thus improve on conventional methods by more accurately predicting recurrence of NSCLC. Example methods and apparatus distinguish patients more likely to experience NSCLC recurrence from patients less likely to experience NSCLC recurrence with an accuracy of at least 0.68 when using TIL density features, or with an accuracy of at least 0.71 AUC when using textural or shape features. Example methods and apparatus may predict NSCLC recurrence with an accuracy of 0.85 AUC in less than one hour when using both textural or shape features and TIL features. Example methods and apparatus thus facilitate a significant, measurable increase in accuracy and speed compared to conventional approaches.

By increasing the accuracy and speed with which NSCLC recurrence is predicted, example methods and apparatus produce the concrete, real-world technical effect of reducing the time required to evaluate medical imagery while increasing the accuracy of the evaluation. Additionally, example apparatus and methods increase the probability that at-risk patients receive timely treatment tailored to the particular pathology they exhibit. Example methods and apparatus may also reduce the number of invasive procedures needed to accurately characterize or plan treatment for NSCLC. The additional technical effect of reducing the expenditure of resources and time on patients who are less likely to benefit from the treatment, or who are less likely to suffer recurrence or disease progression is also achieved. Example methods and apparatus thus improve on conventional methods in a measurable, clinically significant way.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described.

Moreover, less than all the illustrated blocks may be required to implement an example methodology. Blocks may be combined or separated into multiple components. Furthermore, additional and/or alternative methodologies can employ additional, not illustrated blocks.

Like numbers refer to like or similar elements throughout the description of the figures. When an element is referred to as being "connected" to another element, it can be directly connected to the other element or intervening elements may be present. In contrast, when an element is referred to as being "directly connected" to another element, there are no intervening elements present. Other words used to describe the relationship between elements should be interpreted in a like fashion (e.g., "between" versus "directly between," "adjacent" versus "directly adjacent," etc.).

FIG. 1 illustrates an example computerized method 100 for predicting recurrence of NSCLC in a patient demonstrating early stage lung cancer pathology. Method 100 includes, at 110, accessing a diagnostic image of a region of tissue demonstrating NSCLC pathology. Accessing the image may include accessing a digitized whole slide image (WSI) of an H&E stained histopathology slice of a region of tissue demonstrating NSCLC. Accessing the image may also include accessing another type of medical image of a region of tissue demonstrating a different, non-NSCLC pathology. Accessing the image may include retrieving electronic data from a computer memory, receiving a computer file over a computer network, or other computer or electronic based action. In one embodiment, the image is acquired using a Philips High Frequency Whole Slide Scanner. In another embodiment, other types or sizes of images may be employed. The image includes a set of morphological features. The set of morphological features may include a texture feature, a shape feature, or an intensity feature.

Method 100 also includes, at 120, detecting a cellular nucleus represented in the image. In one embodiment, detecting the cellular nucleus represented in the image includes detecting a cellular nucleus using a pixel-level deep learning classifier. The pixel-level deep learning classifier may be, for example, an SVM, or a convolutional neural network. In another embodiment, other types or combinations of pixel-level deep learning classifiers may be employed.

Method 100 also includes, at 130, delineating a segmented nucleus represented in the image. Method 100 delineates the segmented nucleus by segmenting the cellular nucleus from the background of the image. In one embodiment, method 100 delineates the segmented nucleus from the background of the image using a watershed approach. In another embodiment, method 100 delineates the segmented nucleus using a pixel-level convolutional neural network approach, or a region growing approach. In another embodiment, other approaches or combinations of approaches may be employed to delineate nuclei represented in the image.

Method 100 also includes, at 140, extracting a subset of the set of morphological features from the segmented nucleus. The subset includes at least eleven features. In one embodiment, the at least eleven features includes a Haralick feature, an intensity correlation feature, a nuclear texture feature, a Haar feature, a Gabor wavelet, or a color fractal. In another embodiment, the at least eleven features includes other, different features. For example, the at least eleven features may include a shape feature, including a median fractal dimension feature or other shape feature. The at least eleven features may also include graph features. A graph feature may include a feature derived from a cell cluster graph, a Voronoi feature, a Delaunay feature, or a minimum spanning tree.

Method 100 also includes, at 150, providing the subset of features to an automated deep learning classifier. Providing the subset of features to the automated deep learning classifier may include retrieving electronic data from a computer memory, receiving a computer file over a computer network, or other computer or electronic based action. In one embodiment, the deep learning classifier is a QDA classifier. In another embodiment, the deep learning classifier is an LDA classifier, a random forest classifier, or an SVM classifier. In other embodiments, other types, combinations, or configurations of automated deep learning classifiers may be employed.

Method 100 also includes, at 160, receiving, from the automated deep learning classifier, a probability that the region of tissue will experience NSCLC recurrence. The automated deep learning classifier computes the probability that the region of tissue will experience NSCLC recurrence based, at least in part, on the subset of features. Receiving the probability may include retrieving electronic data from a computer memory, receiving a computer file over a computer network, or other computer or electronic based action.

Method 100 further includes, at 170, controlling a computer aided diagnosis (CADx) system to classify the region of tissue as a non-recurrence region or a recurrence region. The CADx system classifies the region of tissue based, at least in part, on the probability or the subset of features. In one embodiment, classifying the region of tissue as a non-recurrence region or a recurrence region includes computing a quantitative continuous image-based risk score. The quantitative continuous image-based risk score is based, at least in part, on the probability or the subset of features.

In one embodiment, method 100 also controls the CADx system to generate a personalized treatment plan for the patient from whom the image was acquired. The personalized treatment plan facilitates the timely, efficient, and accurate application of NSCLC therapy, or other treatment modalities. In one embodiment, the quantitative continuous image-based risk score is employed in conjunction with a threshold score based on a training data set. The training data set may be divided into at least two groups, including those patients who did not experience NSCLC recurrence, and those patients who experienced NSCLC recurrence. The threshold score may be computed such that a percentage of recurrence patients have quantitative continuous image-based risk scores less than the threshold score. The percentage may be, for example, 7%. The threshold score may be user adjustable. Thus, a quantitative continuous image-based risk score less than the threshold score indicates a low-risk of NSCLC recurrence, and example methods and apparatus may generate a personalized treatment plan for the patient after surgery that indicates that no adjuvant chemotherapy should be part of the treatment plan. Quantitative continuous image-based risk scores above the threshold score indicate a higher risk of NSCLC recurrence, suggesting that adjuvant chemotherapy should be part of a personalized treatment plan for the patient. Thus, in one embodiment, upon detecting a quantitative continuous image-based risk score less than a threshold score, method 100 controls the CADx system to generate a personalized treatment plan that indicates no adjuvant chemotherapy should be administered to the patient. Upon detecting a quantitative continuous image-based risk score equal to or greater than the threshold score, method 100 controls the CADx system to generate a personalized treatment plan that indicates that adjuvant chemotherapy should be administered to the patient.

While FIG. 1 illustrates various actions occurring in serial, it is to be appreciated that various actions illustrated in FIG. 1 could occur substantially in parallel. By way of illustration, a first process could access a WSI of a digitized H&E stained pathology slide, a second process could extract a subset of features from the WSI, and a third process could classify the region of tissue represented in the WSI. While three processes are described, it is to be appreciated that a greater or lesser number of processes could be employed and that lightweight processes, regular processes, threads, and other approaches could be employed.

Figure 2:
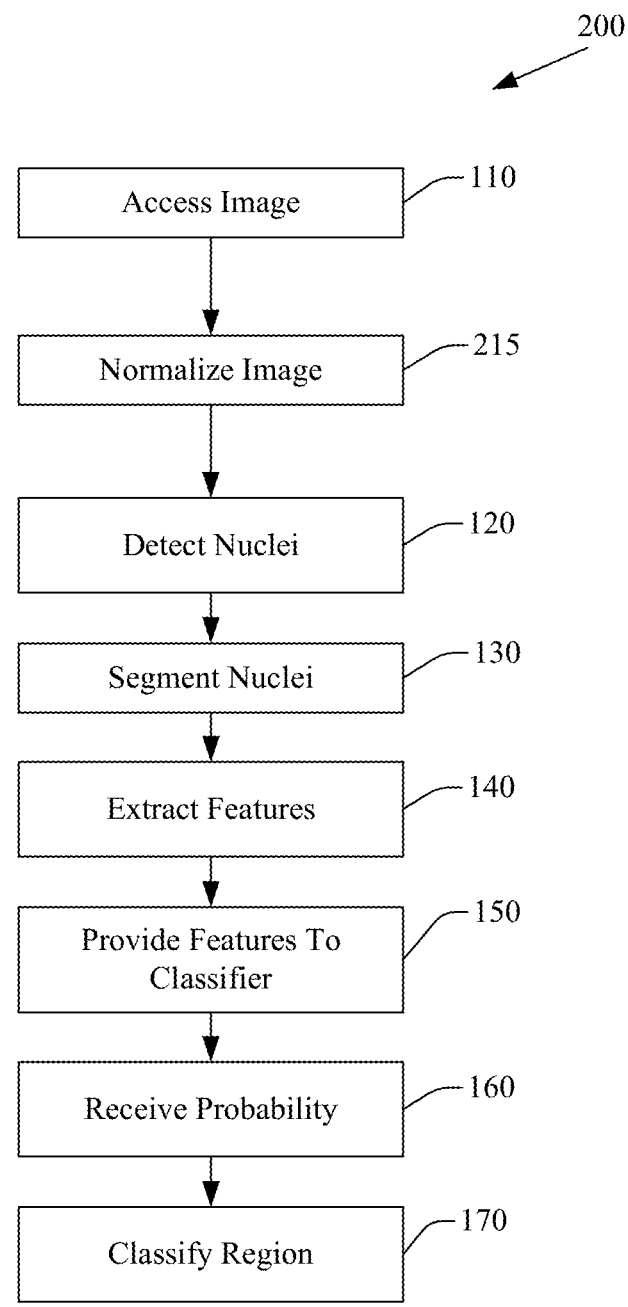
FIG. 2 illustrates an example method for predicting recurrence of NSCLC.

FIG. 2 illustrates an example method 200 for predicting recurrence of NSCLC in a patient demonstrating cancerous pathology. Method 200 is similar to method 100, but includes additional steps and details. Method 200 includes, at 110, accessing an image of a region of tissue demonstrating NSCLC, where the image includes a set of morphological features.

Method 200 also includes, at 215, normalizing the image. In one embodiment, normalizing the image includes color standardizing the image. Color standardizing the image may include non-linearly correcting drift in color within tissue compartments represented in the image. In another embodiment, other normalizing approaches, including stain normalization using sparse autoencoders may be employed.

Method 200 also includes, at 120, detecting a cellular nucleus represented in the image. Method 200 also includes, at 130, delineating a segmented nucleus by segmenting the cellular nucleus from the background of the image. Method 200 also includes, at 140, extracting a subset of the set of morphological features from the segmented nucleus. Method 200 also includes, at 150, providing the subset of features to an automated deep learning classifier. Method 200 also includes, at 160, receiving a probability from the automated deep learning classifier. The probability represents the probability that the region of tissue will experience NSCLC recurrence. Method 200 further includes, at 170, controlling a computer aided diagnosis (CADx) system to classify the region of tissue as a non-recurrence region or a recurrence region. The CADx system classifies the region of tissue based, at least in part, on the probability or the subset of features.

Figure 3:
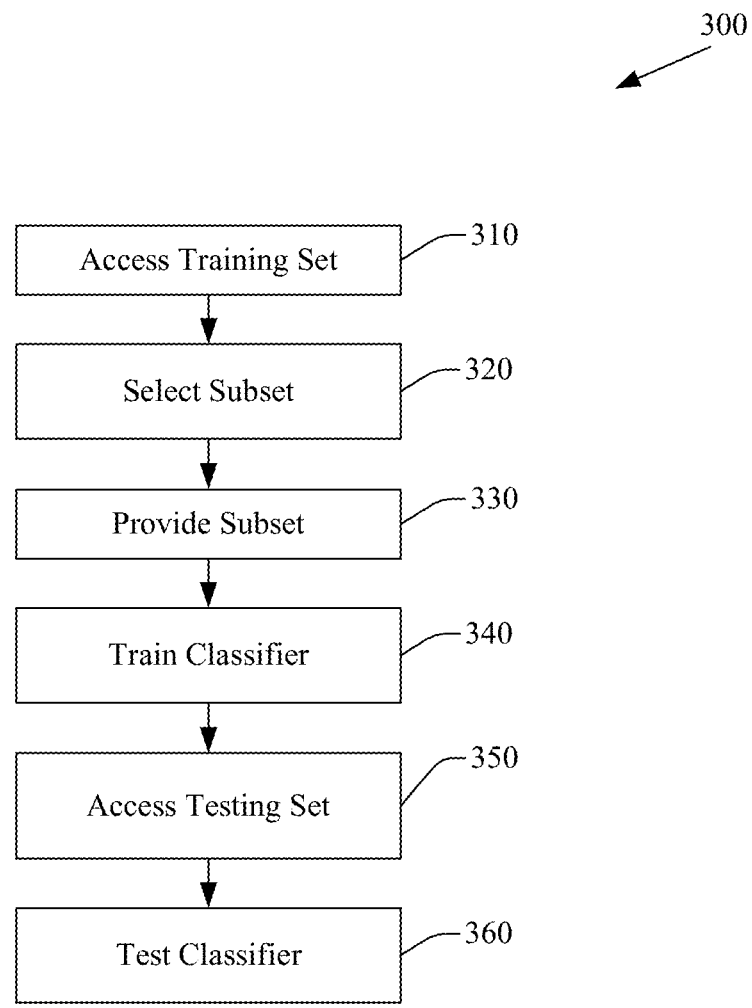
FIG. 3 illustrates an example method for training an automated deep learning classifier.

FIG. 3 illustrates an example method 300 for training an automated deep learning classifier. Method 300 includes, at 310 accessing a training set of digitized WSIs of H&E stained slides of a region of tissue demonstrating NSCLC. A first subset of the training set includes an image of a region of tissue that experienced NSCLC recurrence. A second subset of the training set includes an image of a region of tissue that did not experience NSCLC recurrence. A member of the training set includes a set of features. The set of features includes morphologic features, including texture features, shape features, graph features, or intensity features. A shape feature may be, for example, a median fractal dimension feature or other shape feature.

Method 300 also includes, at 320, selecting, from the training set, a subset of discriminative features. The subset of discriminative features includes a Haralick feature. The subset of discriminative features may also include a shape feature, including a median fractal dimension feature. The subset may also include a graph feature. The subset is selected using quadratic discriminative analysis or linear discriminant analysis. The subset may include at least eleven features. In another embodiment, the subset may be selected using other approaches, or may include another, different number of features. For example, the subset may be selected using principal component analysis (PCA), including PCA-variable importance projection (PCA-VIP) analysis. The subset may include features that are more discriminative than other, non-selected features. A discriminative feature is a feature that demonstrates separation between different classes (e.g. NSCLC recurrence, NSCLC non-recurrence). Example methods and apparatus described herein may quantify a level of discriminability of a feature using, for example, a Bhattacharyya distance or other approaches. The level of discriminability may be user adjustable.

Method 300 also includes, at 330, providing the subset of discriminative features to the automated deep learning classifier. Providing the subset of discriminative features to the automated deep learning classifier may include retrieving electronic data from a computer memory, receiving a computer file over a computer network, or other computer or electronic based action. In one embodiment, the deep learning classifier is a QDA classifier. In another embodiment, the deep learning classifier is an LDA classifier, a random forest classifier, or an SVM classifier. In other embodiments, other types, combinations, or configurations of automated deep learning classifiers may be employed.

Method 300 also includes, at 340, training the automated deep learning classifier with the subset of discriminative features. Training the automated deep learning classifier may include determining an optimal threshold risk score that separates low recurrence rate images from high recurrence rate images based on the training set. The training set may be divided into two groups: those who experience recurrence (Rc+) and those that did not experience recurrence (Rc−). In one embodiment, the optimal threshold may be determined such that 7% of the Rc+ patients have a risk score below the threshold. In another embodiment, other thresholds may be employed.

Method 300 also includes, at 350, accessing a testing set of images. The testing set includes digitized whole slide images of H&E stained slides of a region of tissue demonstrating NSCLC. A first subset of the testing set includes an image of a region of tissue that experienced NSCLC recurrence. A second subset of the testing set includes an image of a region of tissue that did not experience NSCLC recurrence. Accessing the testing set may include retrieving electronic data from a computer memory, receiving a computer file over a computer network, or other computer or electronic based action.

Method 300 further includes, at 360, testing the automated deep learning classifier with the testing set. Testing the automated deep learning classifier may include determining that the classifier has not more than a 50% false positive error rate with the second subset of the testing set, and not more than a 7% false negative error rate with the first subset of the testing set.

In one example, a method may be implemented as computer executable instructions. Thus, in one example, a computer-readable storage medium may store computer executable instructions that if executed by a machine (e.g., computer) cause the machine to perform methods described or claimed herein including method 100, method 200, method 300, or method 800. While executable instructions associated with the listed methods are described as being stored on a computer-readable storage medium, it is to be appreciated that executable instructions associated with other example methods described or claimed herein may also be stored on a computer-readable storage medium. In different embodiments the example methods described herein may be triggered in different ways. In one embodiment, a method may be triggered manually by a user. In another example, a method may be triggered automatically.

Figure 4:
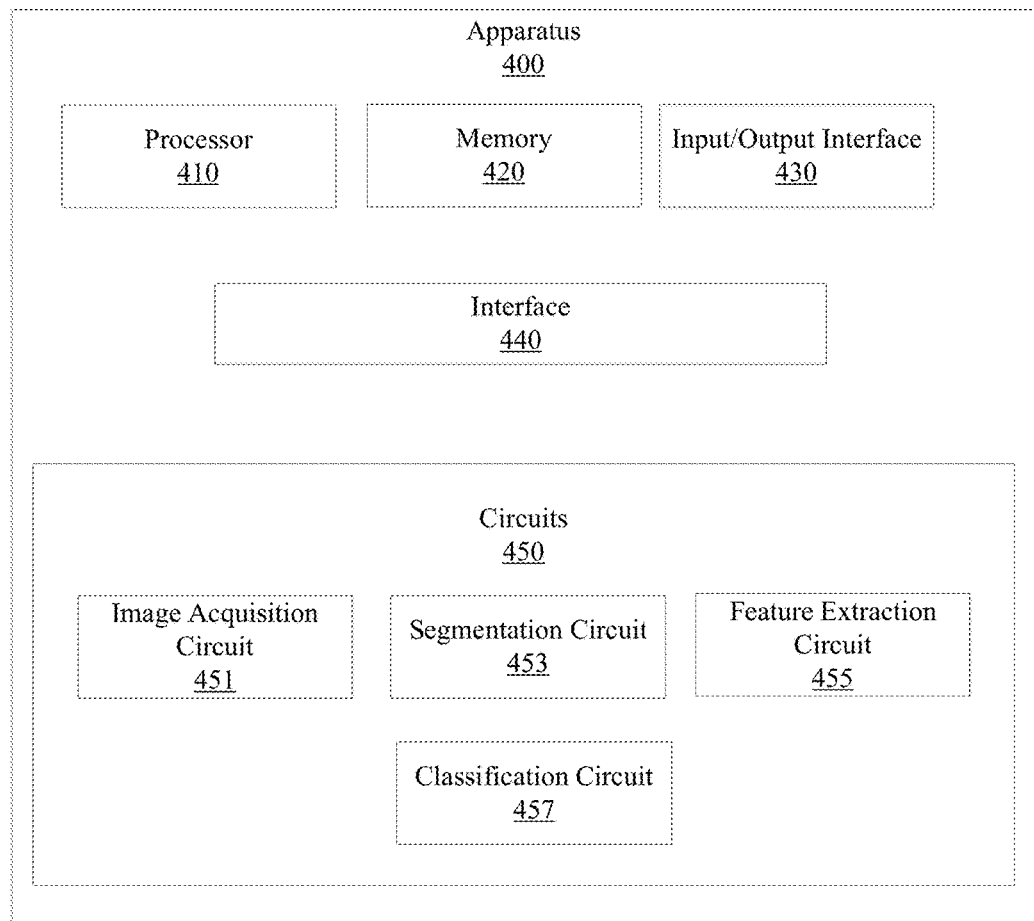
FIG. 4 illustrates an example apparatus that predicts recurrence of NSCLC.

FIG. 4 illustrates an example apparatus 400 for predicting NSCLC recurrence. Apparatus 400 includes a processor 410, a memory 420, an input/output (I/O) interface 430, a set of circuits 450, and an interface 440 that connects the processor 410, the memory 420, the I/O interface 430, and the set of circuits 450. The set of circuits 450 includes an image acquisition circuit 451, a segmentation circuit 453, a feature extraction circuit 455, and a classification circuit 457. In one embodiment, the functionality associated with the set of circuits 450 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of circuits 460 are implemented as ASICs or SOCs.

Image acquisition circuit 451 circuit accesses a set of images demonstrating non-small cell lung cancer (NSCLC). A member of the set of images is a digitized WSI of an H&E stained pathology slice of an NSCLC tumor. The member of the set images includes a set of features, including a shape feature, a texture feature, a graph feature, or an intensity feature. Accessing the image may also include accessing another type of medical image of a region of tissue demonstrating a different, non-NSCLC pathology. Accessing the image may include retrieving electronic data from a computer memory, receiving a computer file over a computer network, or other computer or electronic based action. In one embodiment, the image is acquired using whole slide digital slide scanning of H&E tissue slides via a Philips High Frequency Scanner. Other imaging approaches may be used to generate and access the image accessed by image acquisition circuit 451.

Segmentation circuit 453 detects a cellular nucleus in the member of the set of images. Segmentation circuit 453 detects the cellular nucleus using a using a pixel-level deep learning approach. Segmentation circuit 453 generates a segmented nucleus based on the detected cellular nucleus. In one embodiment, segmentation circuit 453 generates the segmented nucleus using a watershed technique, a pixel-level convolutional neural network, or a region growing approach. Generating the segmented nucleus may include segmenting the cellular nucleus from the background of the member of the set of images. In another embodiment, other approaches may be employed to detect or segment a cellular nucleus represented in the member of the set of images.

Feature extraction circuit 455 extracts a set of discriminative features from the segmented cellular nucleus. In one embodiment, the set of discriminative features includes at least eleven features. The at least eleven features include a Haralick feature, an intensity correlation feature, a nuclear texture feature, a Haar feature, a Gabor wavelet, or a color fractal. In another embodiment, the at least eleven features may include other, different features. For example, the at least eleven features may include a graph feature, or a shape feature, including a median fractal dimension feature or other shape feature. A graph feature may include a feature derived from a cell cluster graph, a Voronoi feature, a Delaunay feature, or a minimum spanning tree. The feature extraction circuit 455 provides the set of discriminative features to the classification circuit 457. Providing the set of discriminative features to the classification circuit 457 may include retrieving electronic data from a computer memory, receiving a computer file over a computer network, or other computer or electronic based action.

Classification circuit 457 computes a probability that the region of tissue will experience NSCLC recurrence. Classification circuit 457 may use QDA, LDA, or a random forest to compute the probability. The probability is based, at least in part, on the set of discriminative features. In one embodiment, classification circuit 457 generates a quantitative continuous image-based risk score based, at least in part, on the probability.

Figure 5:
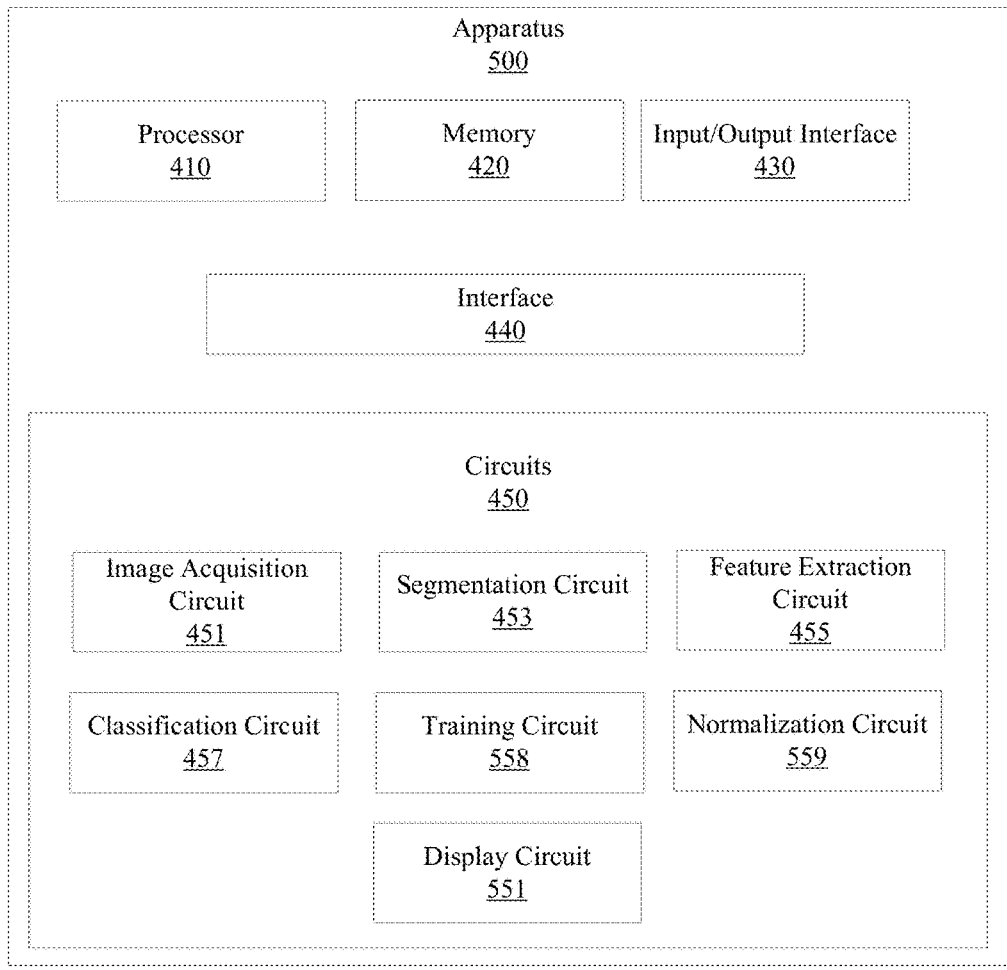
FIG. 5 illustrates an example apparatus that predicts recurrence of NSCLC.

FIG. 5 illustrates an example apparatus 500 that is similar to apparatus 400 but that includes additional circuits and details. Apparatus 500 also includes a display circuit 551. The display circuit 551 may control a CADx system to display a member of the set of images, the probability, or the quantitative continuous image-based risk score on a computer monitor, a smartphone display, a tablet display, or other displays. Displaying the member of the set of images or the probability may also include printing the member of the set of images or the probability. The display circuit 551 may also control the CADx to display an image of a tissue micro array (TMA) of a region of tissue demonstrating NSCLC. The image of the TMA may include morphologic features predictive of NSCLC recurrence. By displaying the member of the set of images, the probability, the quantitative continuous image-based risk score, or the image of the TMA, example apparatus provide a timely and intuitive way for a human pathologist to more accurately classify pathologies demonstrated by a patient, thus improving on conventional approaches to predicting NSCLC recurrence or conventional approaches to planning NSCLC treatment.

Apparatus 500 also includes a training circuit 558. Training circuit 558 trains the classification circuit 457 using a training set of images. Training circuit 558 accesses the training set. Accessing the training set may include retrieving electronic data from a computer memory, receiving a computer file over a computer network, or other computer or electronic based action. The training set may be stored, for example, in memory 420. A first member of the training set represents a region of tissue demonstrating NSCLC that did not experience recurrence. A second member of the training set represents a region of tissue demonstrating NSCLC that experienced recurrence. Training the classification circuit 457 may include determining an optimal threshold risk score that separates low recurrence rate images from high recurrence rate images based on the training set. The training set may be divided into two groups: those who experience recurrence (Rc+) and those that did not experience recurrence (Rc−). In one embodiment, the optimal threshold may be determined such that 7% of the Rc+ patients have a risk score below the threshold. In another embodiment, other thresholds may be employed.

Apparatus 500 also includes an image normalization circuit 559. Image normalization circuit 559 normalizes the set of images using color standardization. Color standardization may include non-linear color drift correction. In another embodiment, other approaches to normalizing the set of images may be employed.

Figure 6:
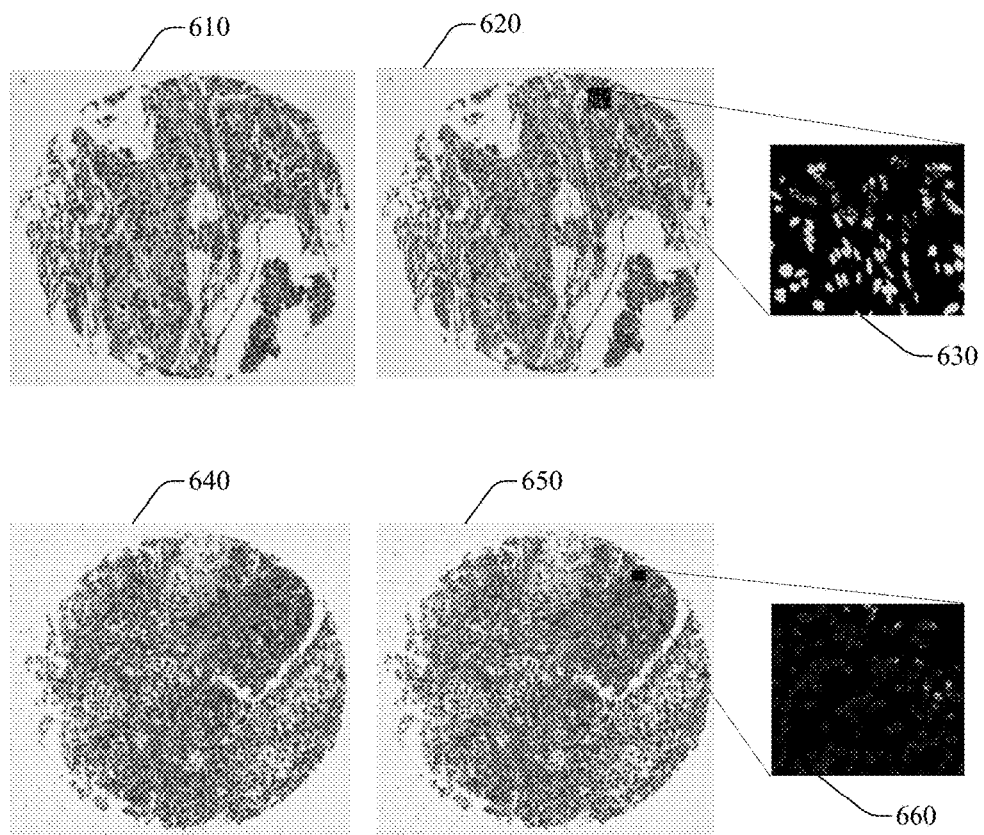
FIG. 6 illustrates sample tissue micro arrays of tissue that experienced non-recurrence or recurrence of NSCLC.

FIG. 6 illustrates example tissue micro arrays (TMA) of regions of tissue demonstrating NSCLC recurrence or non-recurrence. TMA 610 is a sample TMA of a region of tissue demonstrating NSCLC that experienced non-recurrence. TMA 620 represents TMA 610 with a first highlighted tissue section 630. First highlighted section 630 illustrates a Haralick texture feature that expresses a standard deviation intensity correlation of nuclei. TMA 640 is a sample TMA of a region of tissue demonstrating NSCLC that experienced recurrence. TMA 650 represents TMA 640 with a second highlighted tissue section 660. Second highlighted tissue section 660 illustrates a Haralick texture feature indicating an intensity difference with respect to first highlighted tissue section 630.

Figure 7:
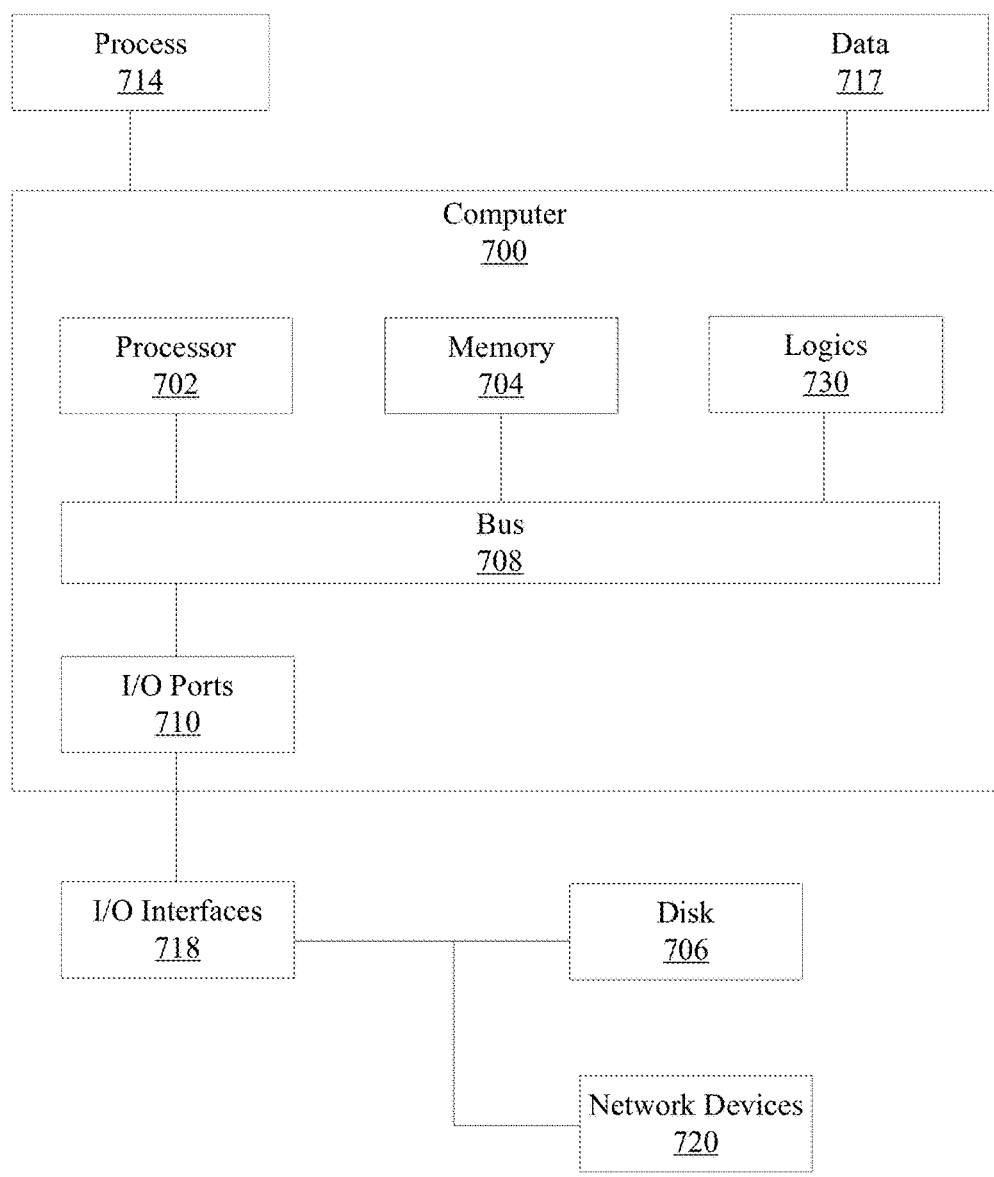
FIG. 7 illustrates an example computer in which example methods and apparatus may operate.

FIG. 7 illustrates an example computer 700 in which example methods illustrated herein can operate and in which example circuits or logics may be implemented. In different examples, computer 700 may be part of a digital whole slide scanner, or may be part of a CADx system.

Computer 700 includes a processor 702, a memory 704, and input/output ports 710 operably connected by a bus 708. In one example, computer 700 may include a set of logics 730 that perform a method of predicting recurrence in a region of tissue demonstrating NSCLC pathology, or a method for training an automated deep learning classifier. Thus, the set of logics 730, whether implemented in computer 700 as hardware or firmware, and/or a combination thereof may provide means (e.g., hardware, firmware) for predicting recurrence of NSCLC in a region of tissue demonstrating NSCLC pathology. In different examples, the set of logics 730 may be permanently and/or removably attached to computer 700. In one embodiment, the functionality associated with the set of logics 730 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of logics 730 are implemented as ASICs or SOCs.

Processor 702 can be a variety of various processors including dual microprocessor and other multi-processor architectures. Memory 704 can include volatile memory and/or non-volatile memory. A disk 706 may be operably connected to computer 700 via, for example, an input/output interface (e.g., card, device) 718 and an input/output port 710. Disk 706 may include, but is not limited to, devices like a magnetic disk drive, a tape drive, a Zip drive, a solid state device (SSD), a flash memory card, a shingled magnetic recording (SMR) drive, or a memory stick. Furthermore, disk 706 may include optical drives like a CD-ROM or a digital video ROM drive (DVD ROM). Memory 704 can store processes 714 or data 717, for example. Disk 706 or memory 704 can store an operating system that controls and allocates resources of computer 700. Data 717 may include, for example, electronic files of WSI images of a region of tissue demonstrating NSCLC.

Bus 708 can be a single internal bus interconnect architecture or other bus or mesh architectures. While a single bus is illustrated, it is to be appreciated that computer 700 may communicate with various devices, logics, and peripherals using other busses that are not illustrated (e.g., PCIE, SATA, Infiniband, 1394, USB, Ethernet).

Computer 700 may interact with input/output devices via I/O interfaces 718 and input/output ports 710. Input/output devices can include, but are not limited to, digital whole slide scanners, a micro-CT machine, a micro-MRI system, an optical microscope, a keyboard, a microphone, a pointing and selection device, cameras, video cards, displays, disk 706, network devices 720, or other devices. Input/output ports 710 can include but are not limited to, serial ports, parallel ports, or USB ports.

Computer 700 may operate in a network environment and thus may be connected to network devices 720 via I/O interfaces 718 or I/O ports 710. Through the network devices 720, computer 700 may interact with a network. Through the network, computer 700 may be logically connected to remote computers. The networks with which computer 700 may interact include, but are not limited to, a local area network (LAN), a wide area network (WAN), or other networks.

Figure 8:
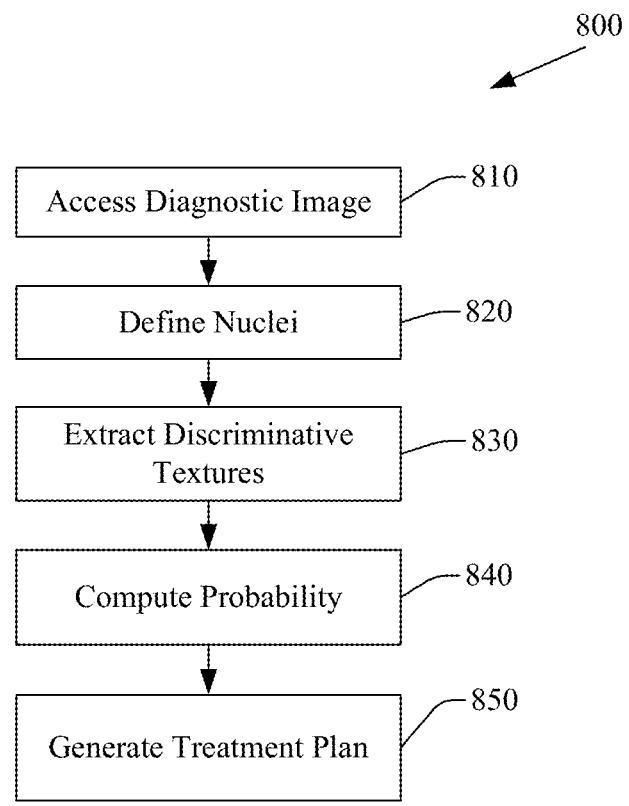
FIG. 8 illustrates an example method for generating a personalized NSCLC treatment plan.

FIG. 8 illustrates an example method 800 for generating a personalized treatment plan for a patient demonstrating NSCLC pathology. Method 800 includes, at 810 accessing a diagnostic image of a region of tissue demonstrating early stage NSCLC. The diagnostic image may be a digitized WSI of an H&E stained slide of a region of tissue demonstrating NSCLC. The diagnostic image includes a set of morphologic features. In another embodiment, the diagnostic image may be acquired using other imaging modalities.

Method 800 also includes, at 820, defining a cellular nucleus represented in the diagnostic image using a watershed segmentation approach. In another embodiment, other approaches may be used to define the cellular nucleus, including a region growing approach, or a pixel-level convolutional neural network. Defining the cellular nucleus may also include segmenting the cellular nucleus from the background of the diagnostic image.

Method 800 also includes, at 830, extracting a set of discriminative features from the cellular nucleus represented in the image. The set of discriminative features includes a texture feature, a shape feature, or an intensity feature. In one embodiment, the set of discriminative features includes at least eleven features. The at least eleven features includes a Haralick feature. The at least eleven features may be selected from among the set of discriminative features based on a threshold level of discriminability.

Method 800 also includes, at 840, computing a probability that the region of tissue will experience NSCLC recurrence. Method 800 may compute the probability using a machine learning classifier. The machine learning classifier may be a QDA classifier, an LDA classifier, or a random forest classifier. The probability is based, at least in part, on the set of discriminative features. In one embodiment, the probability is represented as a quantitative continuous image-based risk score. In another embodiment, other types or combinations of deep learning classifiers may be employed.

Method 800 further includes, at 850, generating a personalized treatment plan. The personalized treatment plan may be based, at least in part, on the probability and the diagnostic image. The personalized treatment plan may indicate adjuvant chemotherapy for the patient from whom the image was acquired, or may contra-indicate adjuvant chemotherapy.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a non-transitory computer-readable medium that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, a data storage device, and other media from which a computer, a processor or other electronic device can read.

"Circuit", as used herein, includes but is not limited to hardware, firmware, software in execution on a machine, or combinations of each to perform a function(s) or an action(s), or to cause a function or action from another circuit, method, or system. Circuit may include a software controlled microprocessor, a discrete logic (e.g., ASIC), an analog circuit, a digital circuit, a programmed logic device, a memory device containing instructions, and other physical devices. Circuit may include one or more gates, combinations of gates, or other circuit components. Where multiple logical circuits are described, it may be possible to incorporate the multiple logics into one physical logic or circuit. Similarly, where a single logical circuit is described, it may be possible to distribute that single logic between multiple logics or circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing computer executable instructions that when executed by a computer control the computer to perform a method for predicting recurrence of non-small cell lung cancer (NSCLC), the method comprising:
    accessing an image of a region of tissue demonstrating NSCLC, where the image includes a set of morphological features;
    detecting a cellular nucleus represented in the image;
    delineating a segmented nucleus by segmenting the cellular nucleus from the background of the image;
    extracting a subset of the set of morphological features from the segmented nucleus;
    providing the subset of features to an automated deep learning classifier;
    receiving, from the automated deep learning classifier, a probability that the region of tissue will experience NSCLC recurrence; and
    controlling a computer aided diagnosis (CADx) system to classify the region of tissue as a non-recurrence region or a recurrence region, based, at least in part, on the probability or the subset of features.

2. The non-transitory computer-readable storage device of claim 1, where the image is a digital whole slide image (WSI) of a hematoxylin and eosin (H&E) stained slide of a region of tissue demonstrating NSCLC.

3. The non-transitory computer-readable storage device of claim 1, where the set of morphological features includes a texture feature, a shape feature, or an intensity feature.

4. The non-transitory computer-readable storage device of claim 2, where detecting a cellular nucleus represented in the image includes detecting a cellular nucleus using a pixel-level deep learning classifier.

5. The non-transitory computer-readable storage device of claim 1, where delineating a segmented nucleus includes segmenting the cellular nucleus from the background of the image using a watershed technique, a pixel-level convolutional neural network approach, or a region growing approach.

6. The non-transitory computer-readable storage device of claim 5, where the subset of the set of morphological features includes at least eleven features.

7. The non-transitory computer-readable storage device of claim 6, where the at least eleven features includes a Haralick feature, an intensity correlation feature, a nuclear texture feature, a Haar feature, a Gabor wavelet, a shape feature, a graph feature, or a color fractal.

8. The non-transitory computer-readable storage device of claim 7, where the automated deep learning classifier is a quadratic discriminant analysis (QDA) classifier.

9. The non-transitory computer-readable storage device of claim 7, where the automated deep learning classifier is a linear discriminant analysis (LDA) classifier, a random forest classifier, or a support vector machine (SVM) classifier.

10. The non-transitory computer-readable storage device of claim 1, where the automated deep learning classifier computes the probability that the region of tissue will experience NSCLC recurrence based, at least in part, on the subset of features.

11. The non-transitory computer-readable storage device of claim 1, where classifying the region of tissue as a non-recurrence region or a recurrence region includes computing a quantitative continuous image-based risk score based, at least in part, on the probability or the subset of features.

12. The non-transitory computer-readable storage device of claim 2, the method further comprising normalizing the image, where normalizing the image includes color-standardizing the image.

13. The non-transitory computer-readable storage device of claim 1, the method further comprising training the automated deep learning classifier.

14. The non-transitory computer-readable storage device of claim 13, where training the automated deep learning classifier includes:

accessing a training set of digitized whole slide images of H&E stained slides of a region of tissue demonstrating NSCLC, where a first subset of the training set includes an image of a region of tissue that experienced NSCLC recurrence, and where a second subset of the training set includes an image of a region of tissue that did not experience NSCLC recurrence, where a member of the training set includes a set of features;

selecting, from the training set, a subset of discriminative features, where the subset of discriminative features includes a Haralick feature, where the subset is selected using quadratic discriminative analysis or linear discriminant analysis;

providing the subset of discriminative features to the automated deep learning classifier;

training the automated deep learning classifier with the subset of discriminative features;

accessing a testing set of digitized whole slide images of H&E stained slides of a region of tissue demonstrating NSCLC, where a first subset of the testing set includes an image of a region of tissue that experienced NSCLC recurrence, and where a second subset of the testing set includes an image of a region of tissue that did not experience NSCLC recurrence;

testing the automated deep learning classifier with the testing set.

15. An apparatus, comprising:
a processor;
a memory;
an input/output interface;
a set of circuits, where the set of circuits includes an image acquisition circuit, a segmentation circuit, a feature extraction circuit, and a classification circuit; and
an interface to connect the processor, the memory, the input/output interface and the set of circuits:
where the image acquisition circuit accesses a set of images of a region of tissue demonstrating non-small cell lung cancer (NSCLC), where a member of the set of images is a digitized whole slide image (WSI) of a hematoxylin and eosin (H&E) stained pathology slice of an NSCLC tumor, where the member of the set images includes a set of features;
where the segmentation circuit detects a cellular nucleus in the member of the set of images, and where the segmentation circuit generates a segmented nucleus based on the detected cellular nucleus;
where the feature extraction circuit extracts a set of discriminative features from the segmented nucleus, and where the feature extraction circuit provides the set of discriminative features to the classification circuit; and where the classification circuit computes a probability that the region of tissue will experience NSCLC recurrence using a quadratic discriminant analysis (QDA), a linear discriminant analysis (LDA), or a random forest, where the probability is based, at least in part, on the set of discriminative features.

16. The apparatus of claim 15, where the segmentation circuit generates the segmented nucleus using a watershed technique, a pixel-level convolutional neural network, or a region growing approach.

17. The apparatus of claim 15, where the set of discriminative features includes at least eleven features, where the at least eleven features include a Haralick feature, an intensity correlation feature, a nuclear texture feature, a Haar feature, a Gabor wavelet, a shape feature, a color fractal, or a graph feature, including a nuclear architecture feature.

18. The apparatus of claim 15, where the set of circuits further comprises a training circuit that trains the classification circuit using a training set of images, where the training circuit accesses the training set, where a first member of the training set represents a region of tissue demonstrating NSCLC that did not experience recurrence, and a second member of the training set represents a region of tissue demonstrating NSCLC that experienced recurrence.

19. The apparatus of claim 15, where the set of circuits further comprises an image normalization circuit that normalizes the set of images using non-linear color drift correction.

20. A method for generating a personalized treatment plan for a patient demonstrating non-small cell lung cancer (NSCLC), the method comprising:
accessing a diagnostic image of a region of tissue demonstrating early stage NSCLC;
defining a cellular nucleus represented in the diagnostic image using a watershed segmentation approach;
extracting a set of discriminative features from the cellular nucleus represented in the image, where the set of discriminative features includes a texture feature, a shape feature, a nuclear architecture feature, or an intensity feature;
computing a probability that the region of tissue will experience NSCLC recurrence using a machine learning classifier, where the machine learning classifier is a quadratic discriminant analysis classifier, a support vector machine (SVM), a linear discriminant classifier, or a random forest classifier, where the probability is based, at least in part, on the set of discriminative features; and
generating a personalized treatment plan based, at least in part, on the probability and the diagnostic image.

* * * * *